United States Patent [19]

Borgonovi

[11] Patent Number: 4,489,425
[45] Date of Patent: Dec. 18, 1984

[54] MEANS AND METHOD FOR DETERMINING RESIDUAL STRESS ON A POLYCRYSTALLINE SAMPLE BY X-RAY DIFFRACTION

[75] Inventor: Giancarlo Borgonovi, Cardiff, Calif.

[73] Assignee: Science Applications, Inc., La Jolla, Calif.

[21] Appl. No.: 453,809

[22] Filed: Jan. 14, 1983

[51] Int. Cl.³ ............................................. G01N 23/20
[52] U.S. Cl. ...................................... 378/72; 364/508
[58] Field of Search ............................ 378/72; 364/508

[56] References Cited

U.S. PATENT DOCUMENTS

| | | | |
|---|---|---|---|
| 2,259,708 | 10/1941 | Schiebold | 378/72 |
| 3,023,311 | 2/1962 | Bessen | 378/72 |
| 3,934,138 | 1/1976 | Bens | 378/72 |
| 4,042,825 | 8/1977 | Ruud | 378/72 |

OTHER PUBLICATIONS

Hayama, et al., "Automation of X-Ray Stress Measurement by Small Digital Computer", 1973, *Symposium on Mechanical Behavior of Materials*, Kyoto, Japan, Aug. 21–23, 1973.

*Primary Examiner*—Alfred E. Smith
*Assistant Examiner*—T. N. Grigsby
*Attorney, Agent, or Firm*—Bruno J. Verbeck; Michael L. Slonecker

[57] ABSTRACT

A polycrystalline sample is irradiated with a collimated beam of substantially monochromatic X-ray radiation to form a diffraction come which extends and expands outwardly from the sample. A substantially planar, two-dimensional, position sensitive detector is disposed across the cone to intercept and thereby form a two-dimensional image of at least a substantial portion of the cone's cross-sectional periphery. A theoretical relationship exists between the shape of the cone's image and the residual stress in the sample such that the image can be analyzed to quantitatively determine the residual stress.

11 Claims, 7 Drawing Figures

MEANS AND METHOD FOR DETERMINING RESIDUAL STRESS ON A POLYCRYSTALLINE SAMPLE BY X-RAY DIFFRACTION

BACKGROUND OF THE INVENTION

This invention pertains to apparatus and methods employed for determining residual stress on polycrystalline samples by X-ray diffraction.

X-ray diffraction has been long established and is the only known, generally accepted, nondestructive method for determining residual stress on polycrystalline samples. When a collimated beam of monochromatic X-ray radiation impinges upon the surface of a polycrystalline sample, a number of cones of diffracted radiation are formed which extend and expand outwardly from the surface of the sample. For one of these cones, the angle by which the incident X-ray beam is deflected is called the scattering angle and is indicated by $2\theta$. The scattering of radiation is due to a particular set of internal crystallographic planes having spacing d, and the diffraction condition is expressed by the so-called Bragg law:

$$\lambda = 2d \sin \theta$$

wherein $\lambda$ is the wavelength of the incident X-ray beam.

The normal to the family of crystallographic planes responsible for the diffraction of the incident X-ray beam forms an angle $\psi$ with the normal to the surface of the polycrystalline sample. The projection of this normal into the plane of the sample's surface forms an angle $\phi$ with a reference direction on said surface. Thus, the normal to the diffracting planes is identified by the angles $\phi$ and $\psi$.

Measurement of the scattering angle $2\theta$ provides a determination of the interplanar spacing d in the direction of the normal to the diffracting planes. If a state of stress is present in the sample, the angle $2\theta$ changes slightly with the orientation of the crystallographic planes and, because this orientation is defined by the angles $\psi$ and $\phi$, it is indicated as $2\theta_{\phi,\psi}$. For the purpose of stress measurements, it is sufficient to measure the variation of the scattering angle with $\phi$ and $\psi$ from a reference value, or $\Delta 2\theta_{\phi,\psi}$.

The determination of the stress at the surface of the sample by X-ray diffraction requires first directing a collimated monochromatic beam of X-rays onto the surface of the sample, and then determining the function $\Delta 2\theta_{\phi,\psi}$ for some values of $\phi$ and $\psi$. It is then possible to derive the stress field in the irradiated area from the function $\Delta 2\theta_{\phi,\psi}$.

In most cases the state of stress is sufficiently defined by a biaxial system of stresses parallel to the surface of the specimen, and the elastic behavior of the sample is substantially isotropic. In this situation the measurement of only two values of $\Delta 2\theta_{\phi,\psi}$ at different angles $\psi$ for constant angle $\phi$ is sufficient to allow the determination of the component of stress in the direction of angle $\phi$.

Two methods are currently employed for determining the function $\Delta 2\theta_{\phi,\psi}$. The first is the so-called diffractometer method which utilizes a narrow-slit detector. The detector is attached to a rotating arm connected for pivotal movement around the point where the incident beam impinges upon the surface of the sample. The diffractometer measures angles directly, and the scattering angle is determined by finding the point of maximum intensity as the detector and arm rotate. The second method is the so-called position sensitive detector method. In this method the detector and its associated electronics provide information concerning the intensity of the radiation falling upon the detector as a function of position. In order to transform the positional information into angular information, the sample-to-detector distance must be very accurately predetermined. Because the variations in $\Delta 2\theta_{\phi,\psi}$ which are produced by stress on the sample are very small, even small errors in the distance measurement can not be tolerated.

Diffractometers and position sensitive detectors of the prior art are basically one-dimensional, i.e.—they are capable of detecting only a relatively minute portion of the diffraction cone periphery. They are also usually designed to perform measurements of $\Delta 2\theta_{\phi,\psi}$ at constant angle $\phi$ and variable angle $\psi$. One drawback associated with these systems is the difficulty encountered in using them to determine residual stress upon polycrystalline samples having surface grains of dimensions which tend to produce spotty diffraction rings on a conventional film exposure, such as, for example, 0.015–0.050 mm grain size in quartz powder using $CuK_\alpha$ X-rays. A still further drawback resides in the fact that only one determination of residual stress in a given direction can be made at a time. For example, the stress component in the direction of the longitudinal axis of the sample can be first determined. Then, a determination of the transverse residual stress component is made by rotating either the sample or detector 90° about an axis perpendicular to the sample surface and while maintaining constant the sample-to-detector distance.

In view of the foregoing drawbacks associated with the prior art, an object of this invention is to provide a means and method for accurately determining mutually orthogonal residual stress components on a polycrystalline sample without the necessity of having to rotate the sample relative to the detector.

Another object of this invention is to provide a means and method wherein accurate prior knowledge of the sample-to-detector distance is not critical for determining the residual stress.

A still further object of this invention is to provide means and method which is usable with polycrystalline materials exhibiting a tendency to produce spotty diffraction rings because of relatively large surface grain dimensions.

SUMMARY OF THE INVENTION

In its most basic form this invention utilizes a planar, two-dimensional, position sensitive detector to intercept and thereby form an image of at least a substantial portion of the cross-sectional periphery of the diffraction cone. The detector and its associated electronics provide the coordinates of the image or curve which results from the intersection of the diffraction cone with the detector plane. Analysis of the obtained curve, i.e.—the cross-sectional periphery of the diffraction cone, is then related to a theoretical relationship, hereafter described, which contains as unknown terms the mutually orthogonal residual stress components. By assuming values for the unknown stress components, and then inserting those assumed values into the various equations describing said relationship, a curve is mathematically generated which can then be compared to the image or curve formed on the detector by the diffraction cone. Various values for each of the stress components are assumed until a curve is generated which most accurately describes the shape of the image or curve on the detector plane. If the sample-to-detector distance is also unknown, an assumed value for the distance can be inserted into the equations and the actual distance determined simultaneously with the residual stress.

DETAILED DESCRIPTION OF THE PREFERRED EMBODIMENT

The method of the present invention, and the apparatus constructed for the practice thereof, is based upon an analysis of the shape of the diffraction ring which results from the intersection of a diffraction cone with a planar detector. As will be more fully explained hereinafter, a theoretical relationship exists between the shape of the diffraction ring and the residual stress values to be determined such that an analysis of the shape of the diffraction ring yields quantitative values for mutually orthogonal residual stress components on the surface of a polycrystalline sample.

Figure 1:
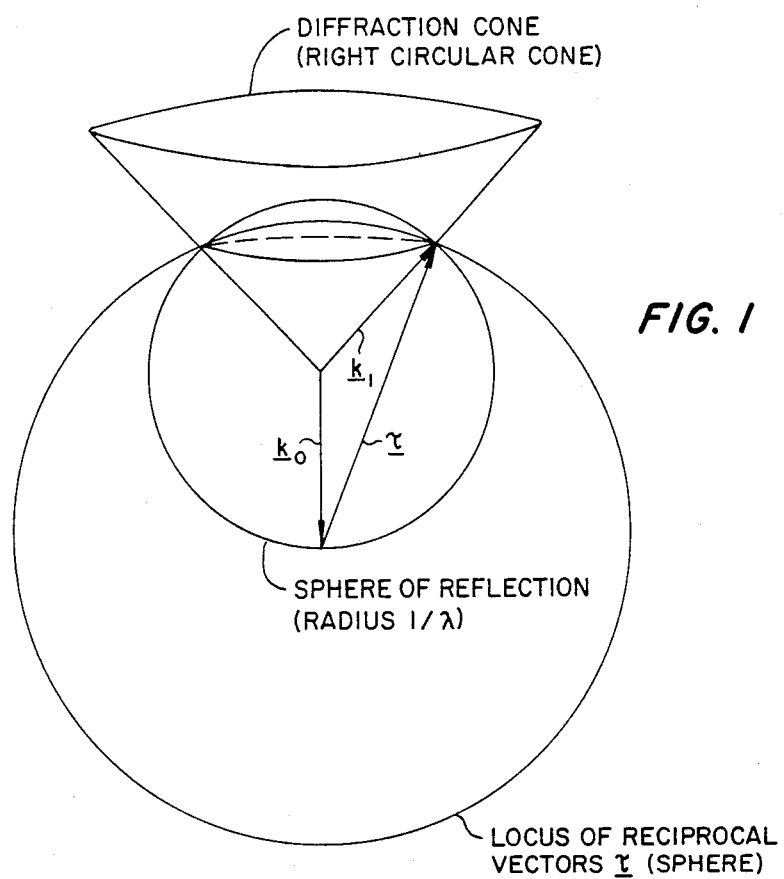
FIG. 1 is representative of the diffraction geometry of a polycrystalline sample under the condition of no stress.
Figure 2:
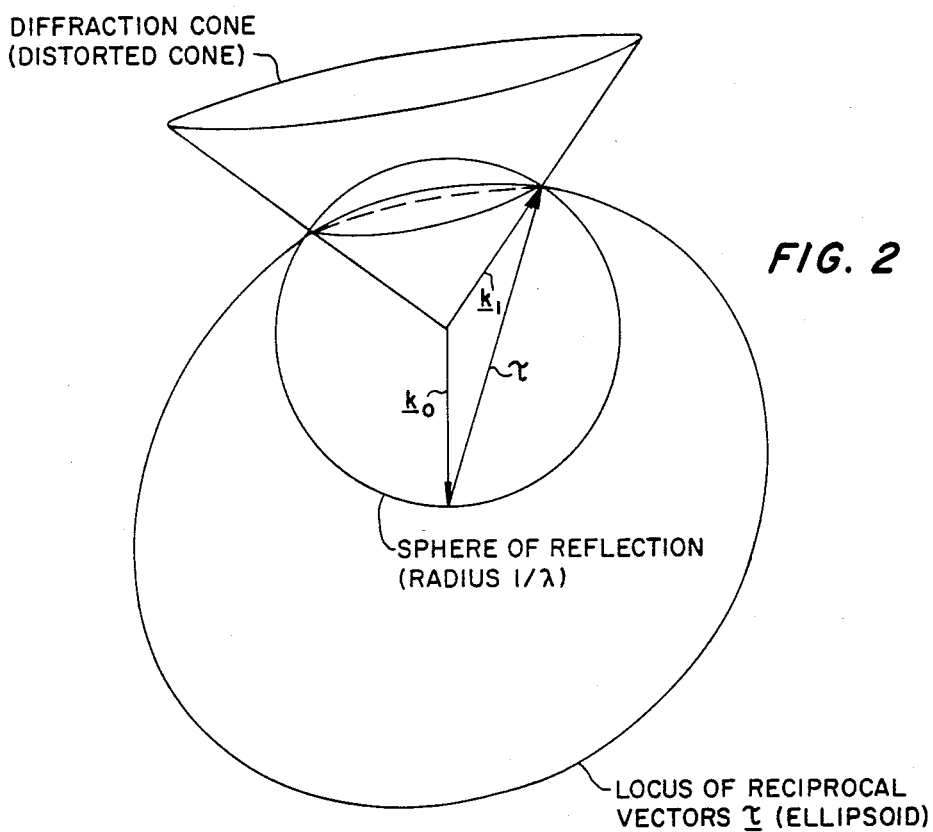
FIG. 2 is representative of the diffraction geometry of a polycrystalline sample under the condition of applied stress.

In the absence of stress, the locus of reciprocal lattice vectors $\tau$ in a polycrystalline sample forms a sphere, and the diffraction cone is a right circular cone which results from the intersection of the sphere of reflection with the locus of reciprocal lattice vectors, as shown in FIG. 1. With stress applied to the polycrystalline sample, the locus of reciprocal lattice vectors forms an ellipsoid, and the diffraction cone becomes distorted since it results from the intersection of the sphere of reflection with the ellipsoid, as shown in FIG. 2. The method and apparatus of this invention advantageously exploit this phenomenon.

Figure 3:
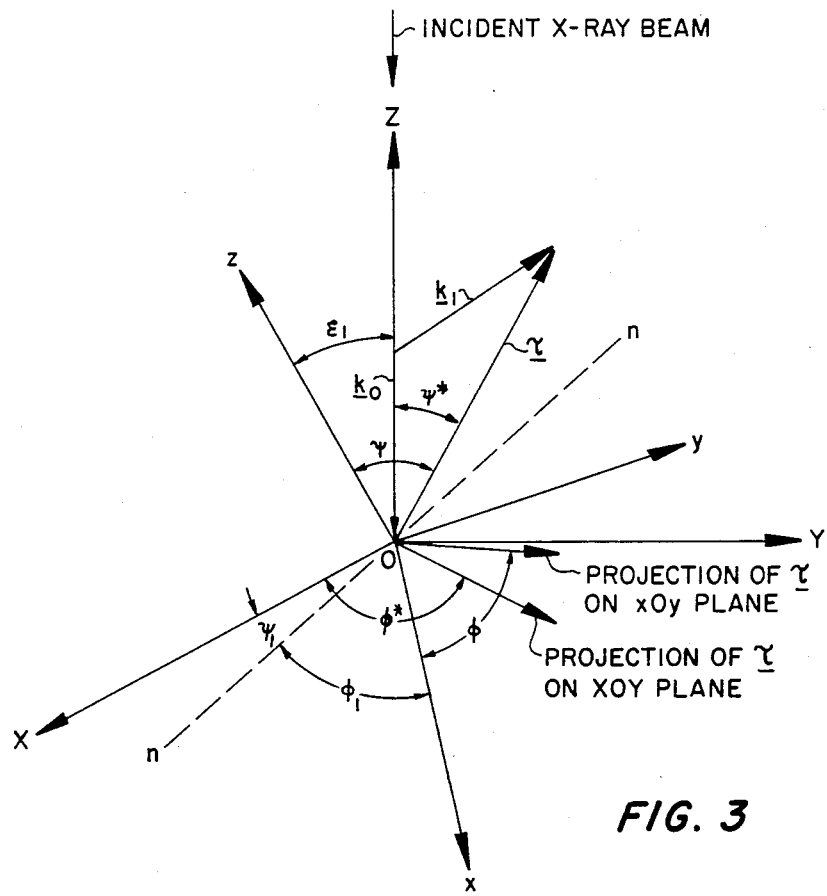
FIG. 3 illustrates the spatial interrelationship between a predetermined reference coordinate system and a coordinate system representative of the polycrystalline sample to be measured for stress.

At the outset is is necessary to understand the reference systems used. Referring to FIG. 3, there is shown a laboratory system OXYZ selected such that the direction of an incident X-ray beam coincides with the negative direction of the Z axis.

Also shown in FIG. 3 is the polycrystalline sample system Oxyz. The axes x and y are taken to be coincident with the direction of the principal residual stresses $\sigma_1$ and $\sigma_2$ on the polycrystalline sample, and the z axis is perpendicular to the sample's surface. The orientation of the sample system with respect to the laboratory system is defined by the three Eulerian angles $\epsilon_1$, $\psi_1$, and $\phi_1$. $\epsilon_1$ is the angular displacement between the Z axis in the laboratory system and the z axis in the sample system. The dashed line n—n represents the nodal line resulting from the intersection of the plane defined by XOY in the laboratory system with the plane defined by xOy in the sample system. $\psi_1$ is the angular displacement between the X axis in the laboratory system and nodal line n—n. This angle is measured within the plane XOY. $\phi_1$ is the angular displacement between the x axis in the sample system and nodal line n—n. This angle lies within the plane xOy.

The components $\tau_i$ of a vector in the sample system are related to its components $\tau_i^*$ in the laboratory system as follows:

$$\tau_i^* = \sum_{i=1}^{3} M_{ik} \tau_k \tag{1}$$

where $M_{11} = \cos\psi_1 \cos\phi_1 + \sin\psi_1 \sin\phi_1 \cos\epsilon_1$ $M_{12} = -\cos\psi_1 \sin\phi_1 + \sin\psi_1 \cos\phi_1 \cos\epsilon_1$ $M_{13} = \sin\psi_1 \sin\epsilon_1$ $M_{21} = -\sin\psi_1 \cos\phi_1 + \cos\psi_1 \sin\phi_1 \cos\epsilon_1$ $M_{22} = \sin\psi_1 \sin\phi_1 + \cos\psi_1 \cos\phi_1 \cos\epsilon_1$ $M_{23} = \cos\psi_1 \sin\epsilon_1$ $M_{31} = -\sin\phi_1 \sin\epsilon_1$ $M_{32} = -\cos\phi_1 \sin\epsilon_1$ $M_{33} = \cos\epsilon_1 \tag{2}$ A reciprocal lattice vector $\tau$ which diffracts the incident X-ray beam is identified by the angles $\phi^*$ and $\psi^*$ in the laboratory system, and by the angles $\phi$ and $\psi$ in the sample system. The angle $\phi^*$ is the angular displacement between the projection of vector $\tau$ on the XOY plane and the X axis. The angle $\phi$ is the angular displacement between the projection of vector $\tau$ on the xOy plane and the x axis. For zero stress the angle $\psi^*$ is constant for different $\phi^*$. This constant value is given by $\psi_o^*$ such that:

$$\cos\psi_o^* = \lambda/2d_o \tag{3}$$

where $\lambda$ is the X-ray wavelength and $d_o$ is the unstressed spacing between adjacent diffracting planes.

The diffraction condition for the vector $\tau$ can be expressed as:

$$\tau = \frac{2}{\lambda} \cos\psi^* \tag{4}$$

In the presence of a stress field characterized by the two principal stresses $\sigma_1$ and $\sigma_2$ ($\sigma_3$ in the z direction is assumed to be zero) the length of the vector $\tau$ is:

$$\tau = \frac{1}{d_o\left[1 + \frac{1+\nu}{\epsilon}\sigma_\phi\sin^2\psi - \frac{\nu}{\epsilon}(\sigma_1 + \sigma_2)\right]} \tag{5}$$

where $\sigma_\phi = \sigma_1 \cos 2\phi + \sigma_2 \sin 2\phi$, E is the Young's modulus, and $\nu$ is the Poisson's ratio.

Combining equations (4) and (5) a relationship is obtained between $\psi^*$, $\phi$, and $\psi$. However, $\phi$ and $\psi$ can be expressed in terms of $\phi^*$ and $\psi^*$, so that a relationship between $\psi^*$ and $\phi^*$ can also be obtained. The derivation of this relationship requires use of equations (1) and (2) and only the final result is set forth. The implicit form of the relationship between $\psi^*$ and $\phi^*$ is:

$$\cos\psi^*[H + Z_1 \sin^2\psi^* + Z_2 \cos^2\psi^* + Z_3 \sin\psi^* \cos\psi^*] = \frac{\lambda}{2d_o} \quad (6)$$

where $$H = 1 - \frac{v}{E}(\sigma_1 + \sigma_2) \quad (7)$$

$$Z_1 = \frac{1+v}{E}(\sigma_1 R_1^2 + \sigma_2 R_2^2)$$

$$Z_2 = \frac{1+v}{E}(\sigma_1 S_1^2 + \sigma_2 S_2^2)$$

$$Z_3 = \frac{2(1+v)}{E}(\sigma_1 R_1 S_1 + \sigma_2 R_2 S_2)$$

$R_1 = M_{11} \cos\phi^* + M_{21} \sin\phi^*$
$R_2 = M_{12} \cos\phi^* + M_{22} \sin\phi^*$
$R_3 = M_{13} \cos\phi^* + M_{23} \sin\phi^*$
$S_1 = M_{31}$
$S_2 = M_{32}$
$S_3 = M_{33}$ For a given value of $\phi^*$, equation (6) is a transcendental equation in $\psi^*$. If $\cos\psi^*$ and $\sin\psi^*$ are expressed in terms of $m = tg\psi^*/2$, a sixth degree equation in $m$ results. Because the stress effect is small, it is convenient to use a perturbation solution of the form:

$$\psi^* = \psi_o^* + \Delta\psi^* \quad (8)$$

When equation (8) is inserted into equation (6), and when second and higher degree terms $\Delta\psi^*$ are neglected, one obtains the solution:

$$\Delta\psi^* = \frac{\cos\psi_o^*(1 - Q_1)}{Q_2 \cos\psi_o^* - Q_1 \sin\psi_o^*}$$

where $Q_1 = H + Z_2 + (Z_1 - Z_2)\sin^2\psi_o^* + Z_3 \sin\psi_o^* \cos\psi_o^*$ $Q_2 = 2(Z_1 - Z_2)\sin\psi_o^* \cos\psi_o^* + Z_3(\cos^2\psi_o^* - \sin^2\phi_o^*)$ (10)

Figure 4:
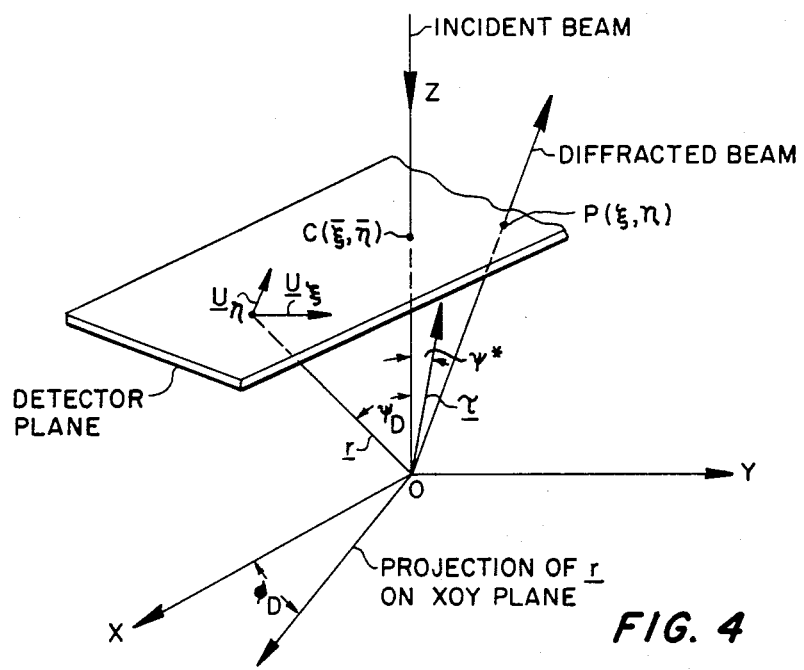
FIG. 4 illustrates the spatial relationship between the predetermined reference coordinate system of FIG. 3 with an X-ray responsive planar detector.

Having just described the spatial and physical interrelationships between the laboratory system OXYZ and the sample system Oxyz, reference is now made to FIG. 4 which illustrates the spatial relationship between the laboratory system and the detector employed in this invention.

For the purpose of describing the diffraction ring image, the detector is identified by a vector r normal to the detector plane, from the origin of the laboratory system to the detector plane, and by two unit vectors $U_\eta$ and $U_\xi$ in the plane of the detector. Vector r is identified by its modulus, i.e.—length, and by the angles $\psi_D$ and $\phi_D$. The angle $\phi_D$ is the angular displacement between the projection of vector r in the XOY plane and the X axis. The angle $\psi_D$ is the angular difference between the Z axis and vector r.

A diffracted beam due to the reciprocal vector $\tau$ identified by the angles $\phi^*$, $\psi^*$ intersects the detector plane at a point P having coordinates $\xi$ and $\eta$. $\xi$ and $\eta$ are obtained by solving the following system of equations:

$$U_{\xi 1}\xi + U_{\eta 1}\eta - \omega k_{11} = -D_1$$

$$U_{\xi 2}\xi + U_{\eta 2}\eta - \omega k_{12} = -D_2$$

$$U_{\xi 3}\xi + U_{\eta 3}\eta - \omega k_{13} = -D_3 \quad (11)$$

where $$D_1 = r\sin\psi_D \cos\phi_D \quad D_2 = r\sin\psi_D \sin\phi_D \quad D_3 = r\cos\psi_D \quad (12)$$

$$k_{11} = \frac{2}{\lambda}\cos\psi^* \sin\psi^* \cos\phi^* = \frac{\sin 2\psi^*}{\lambda}\cos\phi^*$$

$$k_{12} = \frac{2}{\lambda}\cos\psi^* \sin\psi^* \sin\phi^* = \frac{\sin 2\psi^*}{\lambda}\sin\phi^*$$

$$k_{13} = \frac{2}{\lambda}\cos^2\psi^* - 1/\lambda = \frac{\cos 2\psi^*}{\lambda}$$

$$U_{\xi 3} = \sqrt{\frac{1}{1 + (D_3/D_1)^2}} \quad U_{\xi 2} = 0 \quad U_{\xi 1} = -D_3 U_{\xi 3}/D_1$$

$$U_{\eta 3} = \frac{1}{\sqrt{\left(\frac{U_{\xi 3}}{U_{\xi 1}}\right)^2 + \frac{1}{D_2^2}\left(D_1 \frac{U_{\xi 3}}{U_{\xi 1}} - D_3\right)^2 + 1}}$$

$$U_{\eta 2} = \frac{1}{D_2}\left(D_1 \frac{U_{\xi 3}}{U_{\xi 1}} - D_3\right) U_{\eta 3}$$

$$U_{\eta 1} = -\frac{U_{\xi 3}}{U_{\xi 1}} U_{\eta 3}$$

The above equations allow one to calculate the coordinates $\xi$ and $\eta$ on the detector plane. The coordinates of the point C intersection of the incident beam with the detector plane, $\bar{\xi}$ and $\bar{\eta}$, are obtained by solving the system:

$$U_{\xi 1}\bar{\xi} + U_{\eta 1}\bar{\eta} = -D_1$$

$$U_{\xi 2}\bar{\xi} + U_{\eta 2}\bar{\eta} = -D_2 \quad (13)$$

When the sample is moved away from the detector, the intersection of the x-ray beam with the detector plane does not change. Therefore, it is more convenient to use this intersection as the origin in the detector plane and use the following coordinates:

$$\xi' = \xi - \bar{\xi}$$

$$\eta' = \eta - \bar{\eta} \quad (14)$$

The above equations demonstrate that a functional relationship exists between the coordinates $\xi$ and $\eta$ of a point on the diffraction ring on the detector plane. The relationship is expressed in implicit, rather than explicit form. However, it is possible to use the relationship to calculate values of $\xi$ for given values of $\eta$. In other-words, $\xi$ is a function of $\eta$ such that $\xi = f(\eta | \sigma_1, \sigma_2, r)$. This, in turn, allows the calculation of the shape of the distorted diffraction ring for any orientation of the polycrystalline sample and the detector relative to the incident X-ray beam.

The relationship between the coordinates $\xi$ and $\eta$ and the parameters $\sigma_1$ and $\sigma_2$ and r is a relatively complex one, as the above equations demonstrate. By determining the geometrical shape of the diffraction ring defined by the coordinates $\xi$ and $\eta$, it will be readily appreciated that one is thus able to ascertain the values for the parameters $\sigma_1$, $\sigma_2$, and r since the remaining terms in the above equations are all constants for any given system and are readily determined through calibration. A convenient method for determining the shape of the diffraction ring, due to its relative complexity, is a least squares analysis iterated over the sample-to-detector distance only. This will, in turn, yield the stress components $\sigma_1$ and $\sigma_2$.

For an assumed value of r one can calculate, from pairs of coordinates $\xi_i$, $\eta_i$, the pairs of angles $\phi_i^*$, $\psi_i^*$ that will be input to the least squares, using equations (8) and (9) as the analytic form for the fit.

First the analytic form is linearized as follows:

$$\psi^* = \psi_0^* + \Delta\psi^* \Big|_0 + \frac{\partial\psi^*}{\partial\sigma_1}\Big|_0 \Delta\sigma_1 + \frac{\partial\psi^*}{\partial\sigma_2}\Big|_0 \Delta\sigma_2 \quad (15)$$

The derivatives with respect to $\sigma_1$, $\sigma_2$ can be calculated from equations (9) and (10). Once the derivatives have been calculated the problem is a linearized least squares which can be written in matrix form:

$$(\psi^* - \psi_0^*)_{meas} = G\sigma \quad (16)$$

where G is the design matrix. The least squares solution of equation (16) is:

$$\sigma = (G^T G)^{-1} G^T (\psi^* - \psi_0^*)_{meas} \quad (17)$$

Where $G^T$ indicates the transpose matrix of G.

The above estimate of $\sigma_1$ and $\sigma_2$ can be used to recalculate the values of $\psi^*$ and of the derivatives. Iteration is continued until the residual $$R = \sum_i (\psi_i^*{}_{calc} - \psi_i^*{}_{meas})^2 \quad (18)$$

remains constant. This provides an estimate of $\sigma_1$ and $\sigma_2$ for the assumed distance r. The least squares calculation is repeated for several values of r, and the one which gives the minimum residual value is selected. This search-iteration procedure results in convergence upon the best value of the distance and stress components.

Figure 5:
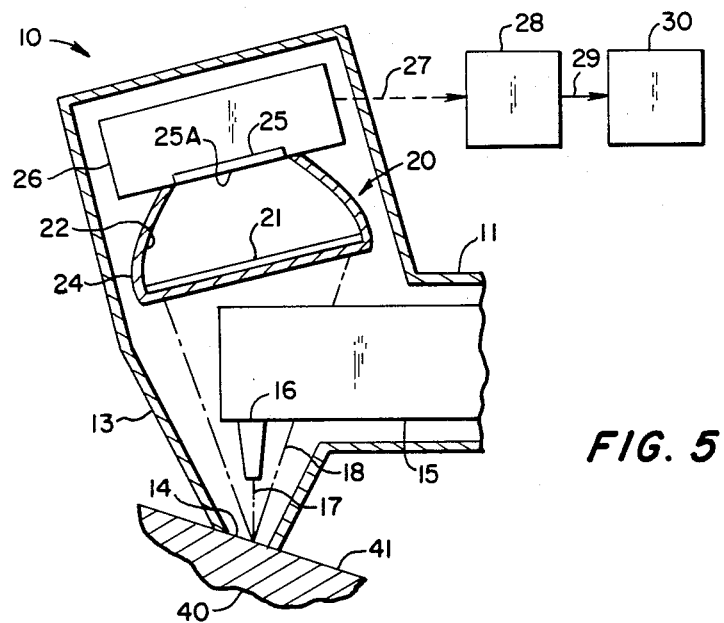
FIG. 5 is a cut-away side view of the preferred embodiment of apparatus constructed in accordance with this invention.

The preferred embodiment of apparatus for implementing the foregoing theoretical relationship is best understood by now referring to FIG. 5. Therein is illustrated an X-ray diffraction apparatus 10 comprising a housing 11. Projecting downwardly from the housing is a conically shaped tubular member 13 which is truncated at one end thereof to form an aperture 14. The shape of the portion of member 13 forming aperture 14 is selected such that when a polycrystalline sample 40 is urged into abutting contact with member 13 across aperture 14, the angle formed between the normal to the surface 41 of sample 40 and the incident X-ray beam 17, i.e.—$\epsilon_1$, is preferrably oblique, typically about 30°.

Supported within housing 11 is an X-ray radiation source comprising an X-ray tube 15 and a collimator 16, said source being positioned to irradiate the surface 41 of sample 40 through aperture 14 with a collimated, substantially monochromatic, beam 17 of X-ray radiation. Because of the polycrystalline structure of sample 40, beam 17 is diffracted therefrom and forms a hollow diffraction cone 18 which extends and expands outwardly from surface 41 within the interior of housing 11.

The X-ray source employed herein is of conventional design, one such suitable X-ray source being the Kevex Model K3050. Said X-ray source includes a target (not shown) formed from, for example, chromium, iron, nickel, molybdenum, or the like. The selection of any particular target material, which material determines the wavelength of the X-ray radiation, of course depends upon the particular polycrystalline material to be analyzed.

Reference numeral 20 generally denotes an X-ray responsive detector utilized in the practice of this invention to form a two-dimensional image of cone 18 in transverse cross-section. Said detector preferably comprises a planar, two-dimensional, position sensitive detector which is responsive along a surface thereof to X-rays of the wavelength contained in cone 18. The term "two-dimensional", as used herein, signifies that the longitudinal and transverse dimensions of the detector's X-ray responsive surface are sufficiently large to enable the formation of a two-dimensional planar image of the line of intersection between the diffraction cone and the detector. It also signifies that, when an X-ray photon strikes the sensitive surface of the detector, a pulse is generated which contains information on the position, in two dimensions, of the detection event.

As shown in FIG. 5, detector 20 preferably comprises a thin layer 21 of scintillating material which emits visible light photons in response to the impingement thereupon of X-ray photons. The scintillating material forming layer 21 can be a mixture of ZnS-CdS, and is commercially available from the Harshaw Company of Solon, Ohio. Layer 21 is also preferably about 2.0 to 5.0 mils thick. Connected to layer 21 is a fiber optic bundle 22 which couples said layer to a photodetector comprising a photocathode 25 and its associated electronics 26. The particular photodetector used herein is the Sealed Sensor Model 3006 manufactured by Surface Science Laboratories, Inc. of Mountain View, Calif. Of course, solid state detectors, such as a CCD or Vidicon photocathode, can also be used. A thin layer 24 of aluminized Mylar or the like, which is transparent to X-rays but opaque to visible light, it provided over layer 21 and fiber optic bundle 22 to prevent extraneous light from falling upon photocathode 25. For improved sensitivity to the shape of diffraction cone 18, the detector is preferably tilted such that layer 21 and photocathode 25 form an angle $\psi_D$ of about 15°.

The impingement of a visible light photon on light-receiving surface 25a of photocathode 25 results in the recordation of a data event of known positional coordinates. The sum total of all such data events thus forms a quite accurate image of the light received by the photocathode, in terms of overall shape, position, and intensity. This data, which can be conceptualized as comprising a highly accurate image of cone 18 both in terms of overall shape and position, is extracted through line 27 by any suitable readout means 28. In the preferred embodiment means 28 comprises the Model 2401 Position Computer manufactured by Surface Science Laboratories, Inc. This particular computer includes an operator selectable analog or digital output. The analog output is, of course, easily connected to any suitable analog display, such as a CRT, printer, etc. However, in order to simplify the quantitative determination of residual stress on sample 40 it is preferred to operate the position computer in the digital output mode, and to direct said digital output through line 29 to a general-purpose digital computer 30. Contained within the memory of computer 30 are all the instructions necessary to act upon the data recorded by detector 20 and to convert that data into quantitative values for residual stress.

While detector 20 of the preferred embodiment is of the scintillating-type, this is not considered to be limiting of the invention. A scintillating-type position sensitive detector is preferred because of its generally more rugged construction. However, assuming adequate precautions are taken to avoid unnecessary jarring of the apparatus 10, then detector 20 can take the form of a proportional-type position sensitive detector such as the Model XD-12 manufactured by Xentronics Company, Inc. of Cambridge, Mass. This detector forms an image of cone 18 in substantially the identical manner as photocathode 25, except that the impingement of the X-ray radiation on the detector is recorded directly without the need to convert the X-ray radiation to radiation of a different wavelength.

Because the X-ray source shown in FIG. 5 is positioned intermediate sample 40 and detector 20, some masking of diffraction cone 18 is present which prevents detection of the entire periphery of said cone. Even so, a sufficient portion of cone 18 is detectable to permit subsequent analysis of the shape thereof.

Figures 6, 7:
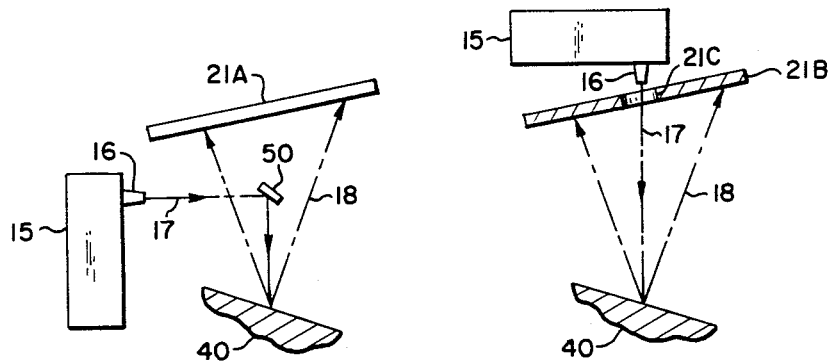
FIG. 6 is a somewhat diagrammatic view of an alternate embodiment of this invention.
FIG. 7 is a somewhat diagrammatic view of another alternate embodiment of this invention.

If it is considered desirable to avoid masking all together, then the alternate forms of this invention shown in FIGS. 6 and 7 maybe advantageously employed. Referring to FIG. 6, reference numeral 21A denotes a planar, two-dimensional, position sensitive detector which can be either of the proportional or scintillating-type. The X-ray source is positioned to one side of detector 21A and sample 40, and beam deflecting means 50, in the form of a monochromating crystal, is interposed between the sample and detector to deflect beam 17 onto sample 40.

FIG. 7 illustrates a planar, two-dimensional, position sensitive detector 21B of the proportional-type. The X-ray source is positioned on the side of detector 21B opposite from sample 40, and an aperture 21C is provided through the detector to permit irradiation of the sample.

As hitherto discussed, the practice of this invention is based upon a theoretical relationship which includes as unknown quantities the values for residual stress $\sigma_1$ and $\sigma_2$. When the apparatus shown in either FIGS. 5, 6, or 7 is energized, a real-time image of the cross-sectional periphery of diffraction cone 18 is obtained and is defined by the curve which results from the intersection of cone 18 with the detector. The method of this invention includes as a necessary step the generation of a family of curves using assumed values for $\sigma_1$ and $\sigma_2$ until such time as a curve is generated which most accurately describes the cone's image. While various mathematical methods may be employed for generating such curves for comparison with the cone's image, this invention preferably employs the least squares solution hereinbefore described. If unknown, the sample-to-detector distance may also be simultaneously determined together with the residual stress.

The means and method shown and described herein, while presently preferred, are merely illustrative of the principles of the invention, and various changes and modifications may be made thereto without departing from the scope and spirit of the invention. Accordingly, all such changes and modifications are contemplated as may come within the scope of the appended claims.

What is claimed is:

1. A method for quantitatively determining residual stress on a sample of polycrystalline material, comprising the steps of irradiating a surface portion of said sample with a collimated beam of substantially monochromatic X-ray radiation to form a cone of diffracted radiation which extends and expands outwardly from said surface portion, forming a two-dimensional image of at least a substantial portion of the cross-sectional periphery of said cone, said image defining the intersection between said cone and a substantially planar X-ray responsive detector, and generating a first geometric curve based upon an assumed value of said stress for comparison with said image.

2. A method as set forth in claim 1 including the step of generating at least one additional geometric curve for comparison with said image if said first curve does not accurately describe said image.

3. Apparatus for quantitatively determining residual stress on a sample of polycrystalline material, comprising a radiant energy source for irradiating a surface portion of said sample with a collimated beam of substantially monochromatic X-ray radiation to form a cone of diffracted radiation which extends and expands outwardly from said surface portion, a substantially planar X-ray radiation responsive detector positioned to form a two-dimensional image of at least a substantial portion of the cross-sectional periphery of said cone, and means for generating at least one two-dimensional geometric curve based upon an assumed value for said residual stress and for comparing said curve with said image.

4. Apparatus as set forth in claim 3 wherein said detector comprises a layer of scintillating material which converts the radiation contained in said cone into radiant energy flux having a different wavelength, and means responsive to said flux for forming an image thereof.

5. Apparatus as set forth in claim 4 further comprising flux coupling means for communicating the flux from said layer to said flux responsive means.

6. Apparatus as set forth in claim 4 further comprising a thin film of material applied on the side of said scintillating layer proximate said sample, said film being substantially opaque towards said flux and substantially transparent towards X-ray radiation.

7. Apparatus as set forth in claim 3 wherein said detector comprises a proportional position sensitive detector.

8. Apparatus as set forth in claim 3 wherein said curve generating means is included within a data processor connected to receive the output from said detector which is representative of said image.

9. Apparatus as set forth in claim 3 wherein said radiant energy source is positioned within said cone intermediate said detector and said sample.

10. Apparatus as set forth in claim 3 wherein said radiant energy source is positioned proximate the side of said detector opposite from said sample.

11. Apparatus as set forth in claim 3 wherein said radiant energy source is positioned outside of said cone intermediate said detector and said sample, said apparatus further comprising means for deflecting said X-ray beam onto said sample.

* * * * *

UNITED STATES PATENT AND TRADEMARK OFFICE
CERTIFICATE OF CORRECTION

PATENT NO. : 4,489,425
DATED : December 18, 1984
INVENTOR(S) : Giancarlo Borgonovi It is certified that error appears in the above-identified patent and that said Letters Patent are hereby corrected as shown below:

Column 4, line 66, the expression for $\sigma_\phi$ should read:

$$\sigma_\phi = \sigma_1 \cos^2\phi + \sigma_2 \sin^2\phi$$

Column 5, line 49, the term "$\phi_o^*$" in the expression for $Q_2$ should read -- $\psi_o^*$ --.

Column 6, line 11, the expressions for $D_1$, $D_2$, and $D_3$ should read:

$$D_1 = r \sin\psi_D \cos\phi_D$$
$$D_2 = r \sin\psi_D \sin\phi_D$$
$$D_3 = r \cos\psi_D$$

Column 6, line 21 the expressions for $U_{\xi 3}$, $U_{\xi 2}$, and $U_{\xi 1}$ should read:

$$U_{\xi 3} = \sqrt{\frac{1}{1 + (D_3/D_1)^2}}$$
$$U_{\xi 2} = 0$$
$$U_{\xi 1} = -D_3 U_{\xi 3}/D_1$$

UNITED STATES PATENT AND TRADEMARK OFFICE
CERTIFICATE OF CORRECTION

PATENT NO. : 4,489,425
DATED : December 18, 1984
INVENTOR(S) : Giancarlo Borgonovi It is certified that error appears in the above-identified patent and that said Letters Patent are hereby corrected as shown below:

Column 6, line 41, the first expression in equation (13) should read:

$$U_{\xi_I}\bar{\xi} + U_{\eta_I}\bar{\eta} = -D_I$$

Column 6, line 51, the expressions in equation (14) should read:

$$\xi' = \xi - \bar{\xi}$$
$$\eta' = \eta - \bar{\eta}$$

Signed and Sealed this

Thirtieth Day of July 1985

[SEAL]

Attest:

DONALD J. QUIGG

Attesting Officer

Acting Commissioner of Patents and Trademarks